United States Patent [19]

Sarumaru et al.

[11] Patent Number: 4,732,884

[45] Date of Patent: Mar. 22, 1988

[54] PROCESS FOR PRODUCING COMPOSITE OXIDE CATALYSTS

[75] Inventors: Kohei Sarumaru; Etsuji Yamamoto; Teruo Saito, all of Ami, Japan

[73] Assignee: Mitsubishi Petrochemical Company Limited, Tokyo, Japan

[21] Appl. No.: 29,647

[22] Filed: Mar. 24, 1987

[30] Foreign Application Priority Data

Mar. 24, 1986 [JP] Japan .................................. 61-65280
Aug. 23, 1986 [JP] Japan ................................ 61-197739
Aug. 23, 1986 [JP] Japan ................................ 61-197740

[51] Int. Cl.$^4$ ........................ B01J 21/08; B01J 23/78; B01J 23/84; B01J 23/88
[52] U.S. Cl. .................................... 502/205; 502/212; 502/215; 502/243; 502/302; 502/304; 502/306; 502/307; 502/311
[58] Field of Search ............... 502/205, 212, 215, 243, 502/302, 304, 306, 307, 311

[56] References Cited

U.S. PATENT DOCUMENTS 4,267,385  5/1981  Umemura et al. .............. 502/311 X
4,541,964  9/1985  Katsumata et al. ............. 502/212 X Primary Examiner—W. J. Shine
Attorney, Agent, or Firm—Oblon, Fisher, Spivak, McClelland & Maier

[57] ABSTRACT

In the production of a Mo-Bi-Na composite oxide catalyst by the process comprising incorporating compounds as respective element sources into a composite and subjecting the composite to heat treatment, a bismuth subcarbonate in which at least a part of required Na has been solid-dissolved is used as a Bi source compound. The activity of the catalyst is significantly improved by introducing Bi and Na in the form of the specified water insoluble compound into the catalyst.

7 Claims, 1 Drawing Figure

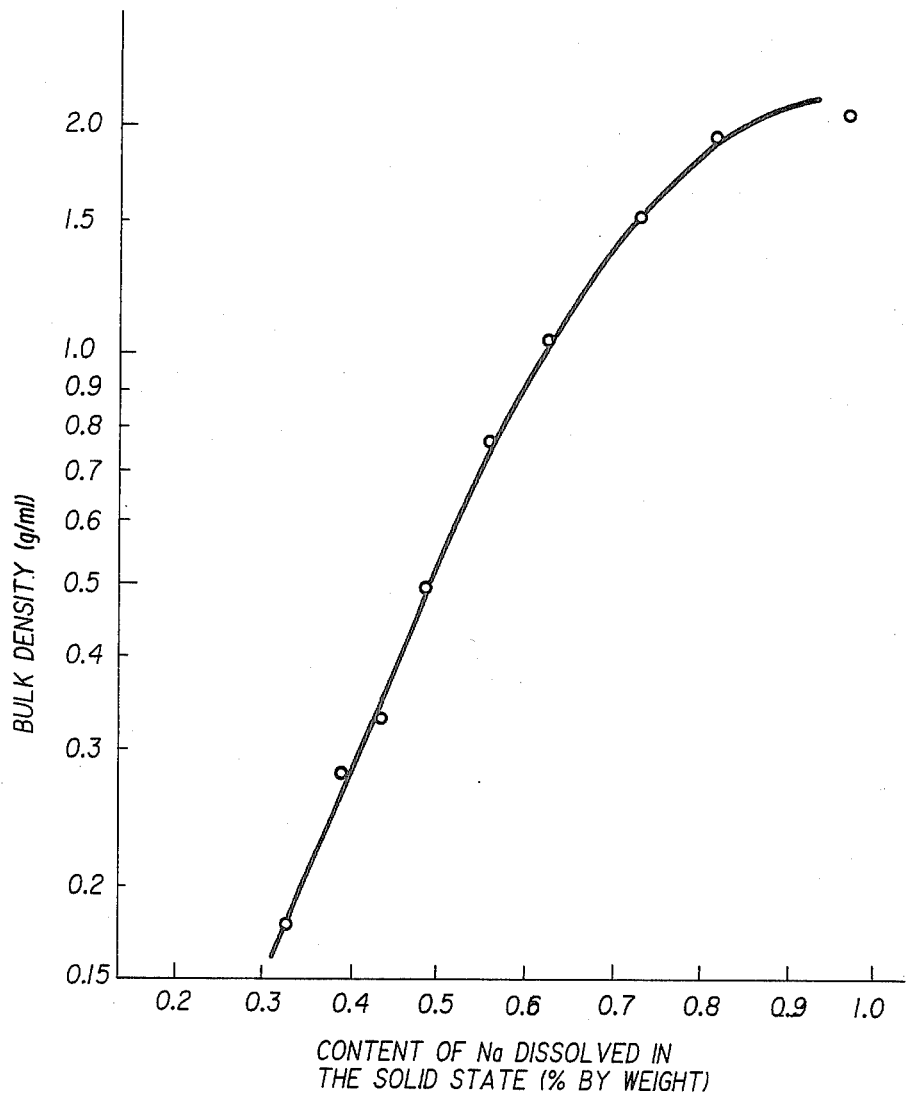

PROCESS FOR PRODUCING COMPOSITE OXIDE CATALYSTS

BACKGROUND OF THE INVENTION

1. Field of the Art

It is well known that Mo-Bi composite oxide catalysts are useful for selective reactions such as vapor phase catalytic oxidation reactions for producing acrolein from propylene or methacrolein from isobutene or tertiary-butanol, a vapor phase catalytic ammoxydation reaction for producing acrylonitrile from propylene or methacrylonitrile from isobutene, and a vapor phase catalytic oxidative dehydrogenation reaction for producing butadiene from butene. It is also well known that these catalysts have widely been put to practical use on an industrial scale.

2. Prior Art

Accordingly, many patent publications with reference to the compositions of Mo-Bi composite oxide catalysts in these various reactions and the processes for producing them are also well known. A part of such publications are: Specifications of Japanese Patent Examined Publication Nos. 3670/64, 1645/73, 4763/73, 17253/73, 3498/74, 41213/80, 14659/81, 23969/81, 52013/81 and 26245/82; and those of Japanese Patent Unexamined Publication Nos. 503/73, 514/73, 52713/73, 54027/73, 57916/73, 20610/80, 47144/80, 84541/80, 76541/84 and 122041/85.

In these patent publications, there are disclosed the addition effects of an alkali metal and/or Tl, but these trace components are handled without any description for their reaction mechanism or the difference between these metals.

Furthermore, all of the aforementioned patent publications relate to Mo-Bi composite oxide. However, all but Japanese Patent Unexamined Publication Nos. 47144/80 and 76541/84, which disclose the preliminary production of a Mo-Bi or W-Bi composite in the course of producing the composite oxide catalysts, use bismuth nitrate as a raw material of Bi in Examples, and in fact, a water soluble bismuth compound, viz. bismuth nitrate or a hydroxide thereof is recommended also in their descriptions. For the purpose of homogeneous dispersion of Bi in the composite oxide catalyst, this indication may be considered acceptable.

SUMMARY OF THE INVENTION

We have found, as a result of detailed researches on the additional effects of alkali metals and Tl and on their mechanisms on incorporating the alkali metal into a Mo-Bi composite oxide catalyst, that distinguishing differences are present in the effects between these metals and their mechanisms. We also have attained, on the basis of these findings, the development of a novel and easy process for producing these Mo-Bi composite oxide catalysts, which process could not have hitherto been obtained or anticipated in the art.

In other words, according to this invention, in its broadest sense, there is provided a process for producing a composite oxide catalyst, wherein a Mo-Bi composite oxide catalyst represented by the following formula is produced by a process comprising incorporating the compounds as respective element sources into a composite in an aqueous system and subjecting the composite to heat treatment, characterized in that use is made as a Bi source of a compound of bismuth carbonate complex of (a) Bi and Na, or (b) Na and X or (c) Bi and X which comprises at least a part of the required Na and/or X $$Mo_aBi_bCo_cNi_dFe_eNa_fX_gY_hZ_iSi_jO_k$$

wherein: X represents Mg, Ca, Zn, Ce and/or Sm; Y represents K, Rb, Cs and/or Tl; Z represents B, P, As and/or W; a-k represent atomic ratios, respectively, and when a equals 12, b=0.5 to 7, c=0 to 10, d=0 to 10, c+d=1 to 10, e=0.05 to 3, f=0.01 to 1, g=0 to 1, h=0.04 to 0.4, i=0 to 3, j=0 to 48 and k is a numeral which satisfies the oxidation state of the other elements.

According to one embodiment of this invention, there is provided a process for producing a composite oxide catalyst (I), wherein a Mo-Bi composite oxide catalyst represented by the following formula (I) is produced by a process comprising incorporating the compounds as respective element sources into a composite and subjecting the composite to heat treatment, characterized in that use is made, as a Bi source, of a compound of bismuth subcarbonate in which at least a part of required Na has been dissolved in the solid state.

$$Mo_aBi_bCo_cNi_dFe_eNa_fY_hZ_iSi_jO_k \quad (I)$$

wherein: Y represents K, Rb, Cs and/or Tl; Z represents B, P, As and/or W; a-f and h-k represent atomic ratios, respectively, and when a equals 12, b=0.5 to 7, c=0 to 10, d=0 to 10, c+d=1 to 10, e=0.05 to 3, f=0.01 to 1, h=0.04 to 0.4, i=0 to 3, j=0 to 48 and k is a numeral which satisfies the oxidation state of the other elements.

According to another embodiment of this invention there is provided a process for producing a composite oxide catalyst, wherein a Mo-Bi composite oxide catalyst represented by the following formula (II) or (III) is produced by a process comprising incorporating the compounds as respective element sources into a composite in an aqueous system and subjecting the composite to heat treatment, characterized in that use is made, as a Bi source, of a compound of bismuth carbonate complex of (a) Bi, Na and X or (b) Bi and X which comprises at least a part of the required Na and X or X:

$$Mo_aBi_bCo_cNi_dFe_eNa_fX_gY_hZ_iSi_jO_k \quad (II)$$

wherein: X represents Mg, Ca, Zn, Ce and/or Sm; Y represents K, Rb, Cs and/or Tl; Z represents B, P, As and/or W; a-k represent atomic ratios, respectively, and when a equals 12, b=0.5 to 7, c=0 to 10, d=0 to 10, c+d=1 to 10, e=0.05 to 3, f=0.01 to 1, g=0.01 to 1, h=0.04 to 0.4, i=0 to 3, j=0 to 48 and k is a numeral which satisfies the oxidation state of the other elements.

According to still another embodiment of this invention there is providd a process for producing a composite oxide catalyst, wherein a Mo-Bi composite oxide catalyst represented by the following formula (II) or (III) is produced by a process comprising incorporating the compounds as respective element sources into a composite in an aqueous system and subjecting the composite to heat treatment, characterized in that use is made, as a Bi source, of a compound of bismuth carbonate complex of Bi and X which comprises at least a part of the required X.

$$Mo_aBi_bCo_cNi_dFe_eNa_fX_gY_hZ_iSi_jO_k \quad (III)$$

wherein X represents Mg, Ca, Zn, Ce and/or Sm; Y represents K, Rb, Cs and/or Tl; Z represents B, P, As and/or W; a-k represent atomic ratios, respectively, and when a equals 12, b=0.5 to 7, c=0 to 10, d=0 to 10, c+d=1 to 10, e=0.05 to 3, f =0 to 1, g=0.01 to 1, h=0.04 to 0.4, i=0 to 3, j=0 to 48 and k is a numeral which satisfies the oxidation state of the other elements.

According to this invention, there are provided catalysts (I), (II) and (III) having high activity and a long serviceable life.

Use of Bi in a non-homogeneous system from the view point of the homogeneous dispersion of ingredient elements being opposed to common sense in the art, the catalyst having such high performance was obtained by introducing Na which has been dissolved in the solid state in a non-homogeneous Bi compound, viz. bismuth subcarbonate into a catalyst, or by introducing the X component as such or in combination with Na into the non-homogeneous Bi compound.

BRIEF DESCRIPTION OF THE DRAWING

In the drawing, the single FIGURE is a graph indicating the relationship between the bulk density of bismuth subcarbonate in which Na has been dissolved in the state of a solid solution and Na content.

DETAILED DESCRIPTION OF THE PREFERRED EMBODIMENT

CATALYST (I)

Analysis of catalyst (I) (1)

The catalyst according to this invention is distinguished from those in the prior art by the feature that compounds as the sources of Bi and Na are specified.

That is, according to this invention, Na is introduced into a catalyst in the form of a solid solution in bismuth subcarbonate, but Na and other alkali metals, namely K, Rb, Cs and Tl, are significantly different from each other in the reaction mechanism in the Mo-Bi composite oxide catalyst, and so are their effects.

It has been found that Na has an effect of increasing the activity of the catalyst and at the same time improving the stability, but K, Rb, Cs and Tl have an effect of increasing the selectivity of the catalyst. As a result of our detailed analysis, it has also been found that the difference of these effects are based on the difference of respective mechanisms. That is, Na is partly present in the form of a solid solution in the crystal of bismuth molybdate which always exists in the Mo-Bi composite oxide catalysts, and thus it is believed that the lattice defect of oxygen in the crystal increases and the mobility of lattice oxygen increases, so that the activity is increased and the stability of bismuth molybdate is improved.

On the other hand, K, Rb, Cs and Tl do not exhibit such a behavior, and it is believed that they solely exist on the borders or the surfaces of respective compounds to bring about improvement of the selectivity. This was presumed to be rational from a comparison of the ionic radii in the monovalent states of these metals and the ionic radius of $(BiO)^+$.

From the elucidation of these relationships, we have deductively come to the conclusion that, if a technique for making more selectively a solid solution of Na in the crystal of bismuth molybdate which exists in a Mo-Bi composite oxide catalyst is developed, a novel performanced catalyst can be developed.

As a result of various basic studies for the purpose of embodiment of the operational hypothesis, it has been found that when a bismuth subcarbonate in which Na is preliminarily dissolved in the form of a solid solution as a raw material of Bi, the objective catalyst can be produced, and that the catalyst thus produced exhibits extremely high performance.

Analysis of catalyst (I) (2)

The result of definite analysis of the catalyst according to this invention is shown below.

First of all, by the use of ammonium molybdate, ferric nitrate, cobalt nitrate, nickel nitrate, bismuth nitrate, boric acid, potassium nitrate and silica (wherein the silica used in this case is silica sol with high purity which is known by the tradename of "SNOWTEX N"), there was produced by a conventional method a catalyst having the following formula (Cat 1).

Cat 1:

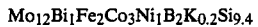

$Mo_{12}Bi_1Fe_2Co_3Ni_1B_2K_{0.2}Si_{9.4}$

When the catalyst thus obtained was examined by X-ray diffraction, the following compounds were identified (the compounds were listed in the sequence of diffraction strength):

$\alpha$-$Bi_2(MoO_4)_3$,
$MoO_3Fe_2(MoO_4)_3$ and
$\beta$-$CoMoO_4$.

Next, by further adding sodium nitrate in the same manner as above, a catalyst having the following formula (Cat 2) was produced.

Cat 2:

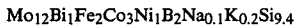

$Mo_{12}Bi_1Fe_2Co_3Ni_1B_2Na_{0.1}K_{0.2}Si_{9.4}$

When the catalyst thus obtained was examined by X-ray diffraction in the same manner as above, the following compounds were identified:

phase X,
$MoO_3$,
$\beta$-$CoMoO_4$,
$\alpha$-$Bi_2(MoO_4)_3$ and
$Fe_2(MoO_4)_3$, wherein phase X represents a compound characterized by $2\theta=28.3°$ in the diffraction of CuK $\alpha$-ray.

Furthermore, by the addition of Na to the system of $Mo_{12}Bi_1Fe_2Co_3Ni_1P_2Cs_{0.1}Si_{9.4}$ having a similar relationship to that of Cat 1 and Cat 2, it was observed that phase was generated.

The reactivities of these catalysts were examined by the use of catalytic oxidation reaction of propylene as a model reaction. As a result, it was found that the catalysts to which Na had been added were more active than those to which Na had not been added.

It was also found that when the content of Na in Cat 2 was increased, phase X was increased, and that phase X was not generated even if the K content in Cat 1 was increased, but the phase X was increased if the K content in Cat 2 was increased.

It was presumed that such observations may reach the following operational hypothesis.

That is, phase X is a compound containing Na, which is possibly the one formed by making a part of Na into a solid solution judging from the Na content.

As a result of detailed examination of X-ray diffraction data of various compounds which can be obtained from respective components of these composite oxide catalysts, it was judged that the compound in this case was one in which (BiO)+ of γ-Bi₂MoO₆ had partly been substituted by Na.

If such an estimation is made it is further presumed that the increase of catalyst activity may be attributed to the generation of lattice defect of oxygen due to the solid solution of Na and the appearance of bismuth molybdate phase.

Furthermore, it was also suspected that all of the Na is not dissolved in solid in Cat 2 but the amount of Na in solid solution is increased by the increase of the K content.

This indicates that the addition effect of K is more effective in the presence of Na.

It is also possible to explain by these presumptions that when a colloidal silica which is known in the art by the tradename "CATALOID SI80P" is used as a raw material of silica for the purpose of producing a catalyst having the same composition as that of Cat 1, appearance of phase X as well as the improvement of the catalyst are observed. The reason is that a CATALOID silica usually contains Na as an impurity and CATALOID SI80P contains Na in an amount corresponding to Na=0.19 based on Si=9.4.

We have conducted researches based on these operational hypotheses to find measures whereby Na can be dissolved in solid more actively and more selectively into the crystal phase of bismuth molybdate.

As a result of various basic researches, we have finally found that the aforementioned objects can be easily accomplished by using as a raw material bismuth subcarbonate in which Na has been preliminarily dissolved in solid by the ordinary method for producing a Mo-Bi composite oxide catalyst.

Bismuth subcarbonate is generally produced by the precipitation method using an aqueous solution of bismuth nitrate and ammonium carbonate, and the production of bismuth subcarbonate in which Na has been dissolved in solid can be easily conducted by the precipitation method with mixing, for example, bismuth nitrate and an aqueous solution of sodium carbonate or sodium bicarbonate. It was also found that change of the Na content in solid solution can be easily accomplished with good reproducibility by changing the concentration of the aqueous bismuth nitrate solution or the concentration of the aqueous sodium salt solution.

It was presumed that the bismuth subcarbonate thus obtained in which a certain amount of Na has been dissolved in solid is obviously in the state of a solid solution because the Na content is not changed even after several times of washing with water and very good correlation is shown between the Na content dissolved in solid and the bulk density of the powder.

When Mo-Bi composite oxide catalysts are produced with bismuth subcarbonates thus obtained and having a variety of Na content, there are provided X-ray diffraction photograms in which the solid solution of Na in bismuth molybdate crystal is presumably generated, and it was proved that excellent reactivity is maintained also in the model experiment by the oxidation reaction of propylene.

Furthermore, in the confirmation of the Na solid solution in these catalysts by means of X-ray diffraction, it becomes difficult to distinguish the peak inherent to it from that in 2θ=28.2° inherent to the γ-Bi₂MoO₆ crystal in the region in which a large amount of Bi is used, but the Na solid solution can be confirmed in some cases by the peak at 2θ=31.8°.

Basic catalyst (I)

The Mo-Bi composite oxide catalysts according to this invention are essentially identical to the conventional ones such as, e.g., those described in the aforementioned patent publications, except for the specified Bi and Na.

Therefore, the Mo-Bi composite oxide catalysts according to this invention can be represented typically by the following formula. The formula is usually used for the expression of composite oxide catalysts and does not necessarily mean the presence of a sole compound represented by this chemical formula.

$Mo_aBi_bCo_cNi_dFe_eNa_fY_hZ_iSi_jO_k$ wherein: Y represents K, Rb, Cs and/or Tl; Z represents B, P, As and/or W; and suffixes of respective elements represent their atomic ratios of the following values.

a: 12,
b: 0.5 to 7,
c: 0 to 10,
d: 0 to 10,
c+d: 1 to 10,
e: 0.05 to 3,
f: 0.01 to 1,
h: 0.04 to 0.4,
i: 0 to 3,
j: 0 to 48 and
k: values satisfying the oxidation degree of other elements

CATALYSTS (II) AND (III)

Analysis of the catalysts (II) and (III)

The catalysts (II) and (III) are distinguished from those in the prior art by the feature that compounds as the source of Bi are specified.

As shown in the above in the analysis of the catalyst (I), Na is significantly different from other alkali metals and Tl in the working mechanism and thus in the effects in the Mo-Bi complex oxide catalysts. We have presented hereinabove a hypothesis that the use of bismuth subcarbonate in which Na has been dissolved in the solid state as the source of Bi and Na to the Mo-Bi based complex oxide catalyst results in formation of bismuth molybdate crystals whose (BiO)+ ions have been replaced by Na+ ions whereby the lattice deficiency of oxygen is increased.

We have followed this hypothesis and assumed that other metals, as such or in combination with Na, can be complexed with bismuth subcarbonate together with Na if the ion radium of the other metals meets the requirement.

Basic catalysts (II) and (III)

The catalysts (II) and (III) in accordance with the present invention are essentially the same as those known in the art such as those shown in the patents or patent publications referred to hereinbefore except for the type of the source of Bi.

The Mo-Bi based complex oxide catalysts (II) and (III) in accordance with the present invention are indicated by the following formulae (II) and (III), which formulae are conventional ones used in indicating complex oxide catalysts and do not necessarily mean a single compound indicated by the formula, respectively.

$Mo_abi_bCo_cNi_dFe_eNa_fX_gY_hZ_iSi_hd\ jO_k$ (II)

wherein: X represents Mg, Ca, Zn, Ce and/or Sm; Y represents K, Rb, Cs and/or Tl; Z represents B, P, As and/or W; a–j represent atomic ratios, respectively, and when a equals 12, b=0.5 to 7, c=0 to 10, d=0 to 10, c+d=1 to 10, e=0.05 to 3, f=0.01 to 1, g =0.01 to 1, h=0.04 to 0.4, i=0 to 3, j=0 to 48 and k is a numeral which satisfies the oxidation state of the other elements.

$$Mo_aBi_bCo_cNi_dFe_eNa_fX_gY_hZ_iSi_jO_k \qquad (III)$$

wherein: X represents Mg, Ca, Zn, Ce and/or Sm; Y represents K, Rb, Cs and/or Tl; Z represents B, P, As and/or W; a–j represent atomic ratios, respectively, and when a equals 12, b=0.5 to 7, c=0 to 10, d=0 to 10, c+d=1 to 10, e=0.05 to 3, f=0 to 1, g=0.01 to 1, h=0.04 to 0.4, i=0 to 3, j=0 to 48 and k is a numeral which satisfies the oxidation state of the other elements.

Production of catalyst (I)

The process for production of the catalyst is essentially identical to the conventional ones except for the consideration on the kinds (and application states) of the compounds as Bi-Na sources.

The production of the Mo-Bi composite oxide catalysts generally comprises incorporating the compounds as respective element sources into a composite in an aqueous system and subjecting the composite to heating.

The phraseology "incorporating the compounds as respective element sources into a composite in an aqueous system" means incorporating aqueous solutions or aqueous dispersions of respective compounds simultaneously or stepwise into a composite. The term "compounds as respective element sources" means not only respective compounds for each of the elements but also includes the compounds containing a plurality of elements (e.g., ammonium phospho-molybdate for Mo and P). The term incorporating means not only incorporating the compounds as respective element sources into a composite but, if necessary, includes the case of incorporating carrier materials such as silica, alumina, silica-alumina, refractory oxides or other materials.

On the other hand, the "heating" aims at the formation of individual oxides and/or composite oxides of the compounds as respective element sources and the thermal treatment of the finally produced composite oxides. The target of the heating is primarily the compounds as respective element sources, but the compounds may be other than the composite of the compounds as all of the element sources. The heating is not necessarily limited to only once. Therefore, the term "heating" used in this specification includes also the case where heating is carried out for each of the compounds as respective element sources and the formation (and, if necessary, the formation of composite oxides) is carried out stepwisely. The phraseology "comprises incorporating and subjecting to heating" means that suitable processes such as drying, grinding, molding and the like in addition of these two processes may be carried out.

According to this invention, at least a part of required Na, preferably most of the Na, more preferably all of the Na is introduced into a catalyst in the state of a solid solution in bismuth subcarbonate. The compound can be readily produced in the same manner as above is preferably used in the form of a powder. The compound as a raw material for producing the catalyst may be particles having a particle size larger than powder but is preferably in the form of small particles in order to carry out the heating process for the thermal diffusion of Bi. The content of Na in solid solution is 0.05 to 1.2% by weight of the bismuth subcarbonate, preferably 0.1 to 1.0% by weight.

A specific example of the process for producing the catalyst according to this invention will now be described. The aforementioned patent publications and the like are now well known in the art, and thus conception of other examples by inference from this specific example should be easy for those skilled in the art.

To an aqueous solution of a molybdenum compound, preferably ammonium molybdate are addd aqueous solutions of iron, cobalt and nickel, preferably nitrates thereof. Next, the compounds of potassium, rubidium, thallium, boron, sodium (all of the required amount is not dissolved in solid into bismuth subcarbonate), phosphorus, arsenic and/or tungsten, preferably water soluble salts thereof are added as aqueous solutions thereof. Furthermore, if necessary, particulate or colloidal silica is added. Then, bismuth subcarbonate powder in which Na has been preliminarily dissolved in solid is added. Slurry thus obtained is amply agitated and then dried.

The dry product in the form of granules or cake is subjected to thermal treatment in a short period at a temperature in the range of 250° to 350° C. In the thermally treated product thus obtained, iron, cobalt and nickel have already formed salts with acidic oxides, but most of the bismuth subcarbonate is maintained in the form of the raw material.

This means that the addition time of the bismuth subcarbonate may be seleced optionally.

The decomposition product thus obtained is formed into a desired shape by any of the methods of extrusion molding, tableting molding, carrying molding and the like.

Next, the product is subjected to final thermal treatment at a temperature condition of 450° to 650° C. for 1 to 16 hours.

Production of catalysts (II) and (III)

The process for production of the catalysts is essentially identical to the conventional ones except for the consideration on the kinds (and application states) of the compounds as the Bi source. Particularly, as the Bi source, a carbonate into which Na, X and Bi or X and Bi have been incorporated is prepared and used.

The carbonate is produced by admixing a predetermined amounts of nitrate of Bi and nitrate of X, adding dropwise the admixture into an aqueous solution of sodium carbonate or sodium bicarbonate to produce a precipitate, which precipitate is then washed with water and is dried upon necessity.

Production of the Mo-Bi based complex oxide catalysts comprises, in general, incorporating the compounds as respective element sources into a composite in an aqueous system and subjecting the composite to heat treatment.

The expression "incorporating the compounds as respective element sources in an aqueous system" means that aqueous solutions or aqueous dispersions of the compounds are incorporated in a single step or stepwise. The expression "the compounds as respective element sources" includes not only compounds each for each element but also compounds which contain a plurality of elements in a single compound such as ammonium phosphomolybdate when it comes to Mo and P. The expression "incorporating" includes not only incorporating only the compounds as respective element sources but also incorporating a support or carrier material such as alumina, silica, alumina, or a refractory oxide in addition to the compounds as respective element sources.

The "heating", on the other hand, is to produce each oxide and/or a complex oxide of the compounds as the source elements and/or to produce each oxide and/or a complex oxide of the complex compounds formed by the incorporating step and/or to subject the final complex oxide to heat treatment. The heating is not restricted to the heating of the composite of the compounds as the source elements or to the heating carried out once. Accordingly, the "heating" in accordance with the present invention includes the case where each of compounds as element source is heated as such or stepwise from one to another in the presence of the prior-heated one to form each oxide or complex oxides. The expression "comprising incorporating ... and subjecting ... to heat treatment" includes the case where suitable steps other than the step of the incorporating and the subjecting to heat treatment such as drying, pulverizing, forming and the like are used.

According to the present invention, the compounds as the Bi source are water-insoluble bismuth subcarbonate containing Na and/or an element which is Mg, Ca, Zn, Ce and/or Sm. This is used preferably in the form of powder. The subcarbonate can be made up of particles of larger particle size than that in powder, but smaller particles or a form of powder are/is preferable in view of thermal diffusion of the element included during the heating step. Accordingly, pulverizing is preferably practiced to the subcarbonate of particles of a larger particle size before the heating step.

The process for producing the catalyst (II) or (III) is exemplified hereinbelow. In view of the state of the act in which the patent publications referred to hereinbefore are included, it would be easy for those skilled in the art to modify the example given below.

To a suitable molybdenum compound, preferably ammonium molybdate, in an aqueous solution, is added compounds of iron, cobalt and nickel, preferably each nitrate, in an aqueous solution. Further is added compounds of sodium, potassium, rubidium, thallium, boron, phosphorus, arsenic and/or tungsten, preferably water-soluble compounds, in an aqueous solution. Granular or colloidal silica is added upon necessity. Then, powder of bismuth subcarbonate into which Na and X or X have or has been incorporated is then added. The bismuth subcarbonate into which Na and X or X have or has been incorporated is produced, as shown hereinbefore, by admixing water soluble compounds, preferably nitrates, of Bi, and of Mg, Ca, Zn, Ce and/or Sm, in the form of an aqueous solution, pouring dropwise the admixture to an aqueous solution of sodium carbonate or sodium bicarbonate to form a slurry, subjecting the slurry to filtration, and washing and drying the filtrate.

The slurry thus obtained is fully agitated, and dried.

The dried cake which can sometimes be in the form of granules is subjected to heat treatment in air at a temperature of 250° to 3502 C. for a short time. In the product obtained in one actual practice, Fe, Co and Ni were found to form salts with acidic oxides while most of the bismuth subcarbonate was as it had been. This means that bismuth subcarbonate can be added at any step desired.

The product thus obtained from the heat treatment, will be processed into any forms by means of extrusion, tabletting or any other forming operation.

The formed product will then be subjected to the final heat treatment at a temperature of preferably 450° to 650° C. for 1 to 16 hours.

The production of the Mo-Bi composite oxide catalysts generally comprises incorporating the compounds as respective element sources into a composite in an aqueous system and subjecting the composite to heating.

Use of catalyst

The composite oxide catalyst (I), (II) and (III) according to this invention can be used for various vapor phase catalytic oxidation reactions carried out in the presence of molecular oxygen.

The examples of the vapor phase catalytic oxidation reaction mentioned in this specification include the reaction for producing acrolein or methacrolein from propylene, isobutene or t-butanol, the reaction for producing acrylonitrile or methacrylonitrile from propylene or isobutene in the presence of ammonia, and the reaction for producing butadiene from butene and the like.

EXPERIMENTAL EXAMPLES

Example A-1

In 400 ml of pure water is dissolved 94.1 g of ammonium paramolybdate under heating. Next, 7.18 g of ferric nitrate, 25.8 g of cobalt nitrate and 38.7 g of nickel nitrate are dissolved in 60 ml of pure water under heating. These two solutions are slowly mixed with each other by ample agitation.

To the mixed solution is added a solution in which 0.85 g of borax and 0.36 g of potassium nitrate have been dissolved in 40 ml of pure water under heating, and the mixture is agitated well. Then, 57.8 g of bismuth subcarbonate in which 0.57 g of Na has been dissolved in solid and 64 g of silica are added to the mixture and mixed with agitation. Next, after heat drying of the slurry, it is subjected to thermal treatment at 300° C. for 1 hour in an aerial atmosphere. The solid body is formed into tablets of 5 mm in diameter and 4 mm in height by the use of a small scale molding machine and then calcined in a muffle furance at 500° C. for 4 hours to obtain a catalyst.

The composition ratios of the metal ingredients of the catalyst calculated from the raw materials charged are illustrated by the composite oxide having the following atomic ratios.

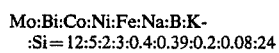
Mo:Bi:Co:Ni:Fe:Na:B:K-
:Si=12:5:2:3:0.4:0.39:0.2:0.08:24

This catalyst in an amount of 20 ml is charged into a stainless steel reaction tube provided with a jacket for a nitrate heating media and having an internal diameter of 15 mm, and raw material gas comprising 10% of propylene concentration, 17% of steam concentration and 73% of air concentration is passed through the tube with a contact period of 2.3 seconds under atmospheric pressure.

At a reaction temperature of 310° C., the following results of reaction were obtained in an actual instance of practice.

Conversion of propylene: 98.7%
Yield of acrolein: 90.6%
Yield of acrylic acid: 4.5%
Total yield: 95.1%

Comparative Example A-1

In 400 ml of pure water was dissolved 94.1 g of ammonium paramolybdate under heating. Next, 7.18 g of ferric nitrate, 25.8 g of cobalt nitrate and 38.7 g of nickel nitrate were dissolved in 60 ml of pure water under heating. These two solutions are slowly mixed with each other by thorough mixing.

The mixed solution was added a solution in which 0.85 g of borax, 1.09 g of sodium nitrate and 0.36 g of potassium nitrate had been dissolved in 40 ml of pure water under heating, and the mixture was amply agitated. Then, 57.8 g of bismuth subcarbonate obtained from an aqueous solution of bismuth nitrate and ammonium bicarbonate by the precipitation method and having no Na dissolved in solid and 64 g of silica were added to the mixture and mixed with agitation. A catalyst was thereafter produced as in Example A-1.

The composition ratios of metal components of the catalyst calculated from the raw materials charged were the same as in Example A-1.

Oxidation reaction of propylene was carried out under the same conditions as in Example A-1 by the use of 20 ml of the catalyst.

At a reaction temperature of 310° C., the following results of reaction were obtained.
  Conversion of propylene: 95.9%
  Yield of acrolein: 87.1%
  Yield of acrylic acid: 5.3%
  Total yield: 92.4%

Comparative Example A-2

In 400 ml of pure water was dissolved 94.1 g of ammonium paramolybdate under heating. Next, 7.18 g of ferric nitrate, 25.8 g of cobalt nitrate and 38.7 g of nickel nitrate were dissolved in 60 ml of pure water under heating. These two solutions were slowly mixed with each other by ample agitation.

To the mixed solution was added a solution in which 0.85 g of borax, 0.38 g of sodium nitrate and 0.36 g of potassium nitrate had been dissolved in 40 ml of pure water under heating, and the mixture was amply agitated. Then, a solution in which 12 ml of nitric acid had been added to 98 ml of pure water and to this solution had been dissolved 108 g of bismuth nitrate was added with ample agitation.

Then, 64 g of silica is added to the mixture and mixed with agitation. A catalyst was obtained in the same manner as in Example A-1 by forming the mixture and calcining the formed product in a muffle furnace at 480° C. for 8 hours.

The composition ratios of the metal ingredients of the catalyst calculated from the raw materials charged are illustrated by the composite oxide having the following atomic ratios.

$Mo:Bi:Co:Ni:Fe:Na:B:K:Si = 12:5:2:3:0.4:0.2:0.2:0.08:24$

Using this catalyst in an amount of 40 ml in the same reactor as in Example A-1, oxidation reaction of propylene was carried out by passing the raw material gas comprised of 12% of propylene concentration, 10% of steam concentration and 78% of air concentration through the reactor with a contact period of 4.2 seconds under atmospheric pressure.

At a reaction temperature of 290° C., the following results of reaction were obtained.
  Conversion of propylene: 97.2%
  Yield of acrolein: 88.0%
  Yield of acrylic acid: 4.1%
  Total yield: 92.1%

Example A-2

In 400 ml of pure water is dissolved 94.1 g of ammonium paramolybdate under heating. Next, 18.0 g of ferric nitrate and 51.6 g of cobalt nitrate are dissolved in 60 ml of pure water under heating. These two solutions are slowly mixed with each other by ample agitation.

To the mixed solution is added a solution in which 0.90 g of potassium nitrate is dissolved in 40 ml of pure water and further 4.35 g of orthophosphoric acid is added, and the mixture is thoroughly agitated. Then, 23.1 g of bismuth subcarbonate in which Na is dissolved in solid in an amount of 0.72% by weight and 32 g of silica are added, and the mixture is mixed with agitation. In an actual instance of practice, a catalyst having the following composition was produced thereafter as in Example 1.

$Mo:Bi:Co:Fe:P:Na:K:Si = 12:2:4:1:1:0.15:0.2:12$

When the catalyst was subjected to the evaluation of oxidation reaction of propylene in the same manner as in Example A-1, the following results were obtained at a reaction temperature of 310° C.
  Conversion of propylene: 98.2%
  Yield of acrolein: 89.7%
  Yield of acrylic acid: 4.1%
  Total yield: 93.8%

Example A-3

In 400 ml of pure water is dissolved 94.1 g of ammonium paramolybdate under heating. Next, 5.8 g of ammonium paratangstate is added, and the mixture is agitated.

On the other hand, 7.18 g of ferric nitrate, 38.7 g of cobalt nitrate and 25.8 g of nickel nitrate are dissolved in 60 ml of pure water under heating. These two solutions are slowly mixed with each other with ample mixing. Then, to the mixed solution is added a solution in which 0.85 g of borax and 0.71 g of thallium nitrate have been dissolved in 40 ml of pure water with heating, and the mixture is thoroughly agitated. Then, 57.8 g of bismuth subcarbonate in which Na has been dissolved in solid in an amount of 0.45% by weight and 32 g of silica are added, and the mixture is mixed with agitation. In an actual instance of practice, a catalyst having the following composition was produced thereafter as in Example A-1 hereafter.

$Mo:W:Bi:Co:Ni:Fe:Na:B:Tl:Si = 12:0.5:5:3:2:0.4:0.33:0.2:0.06:12$

When the catalyst was subjected to the evaluation of oxidation reaction of propylene in the same manner as in Example A-1, the following results were obtained at a reaction temperature of 310° C.
  Conversion of propylene: 98.4%
  Yield of acrolein: 90.1%
  Yield of acrylic acid: 4.8%
  Total yield: 94.9%

EXAMPLE A-4

In a stainless-steel reaction tube having an internal diameter of 15 mm and equipped with a jacket for a nitrate heating media was charged 60 ml of the catalyst described in Example A-1, and ammoxydation reaction was carried out by passing a raw material gas comprised of 4.3% of propylene concentration, 10.1% of ammonia concentration, 24.2% of steam concentration and 51.4% of air through the tube with a contact time for 2.9 seconds.

At 330° C. of the reaction temperature, the following results were obtained:
Conversion of propylene: 69.7%
Yield of acrylonitrile: 65.7%
Selectivity of acrylonitrile: 94.2%

Comparative Example A-3

Using the same catalyst as described in Example A-2, ammoxydation reaction of propylene was carried out under the same conditions as in Example A-4.

At 330° C. of the reaction temperature, the following results were obtained:
Conversion of propylene: 47.7%
Yield of acrylonitrile: 40.8%
Selectivity of acrylonitrile: 85.7%

Example B-1

In 400 ml of pure water is dissolved 94.1 g of ammonium paramolybdate under heating. Next, 7.18 g of ferric nitrate, 25.8 g of cobalt nitrate and 38.7 g of nickel nitrate are dissolved in 60 ml of pure water under heating. These two solutions are slowly mixed with each other by ample agitation.

To the mixed solution is added a solution in which 0.85 g of borax and 0.36 g of potassium nitrate have been dissolved in 40 ml of pure water under heating, and the mixture is agitated well. Then, 58.1 g of white bismuth subcarbonate in which 0.50% by weight of Na and 0.3% by weight of Ca have been complexed and 32 g of silica are added to the mixture and mixed with agitation. Next, after heat drying of the slurry, it is subjected to thermal treatment at 300° C. for 1 hour in an aerial atmosphere. The particulate solid is obtained into tablets of 5 mm in diameter and 4 mm in height by the use of a small scale molding machine and then calcined in a muffle furnace at 500° C. for 4 hours to obtain a catalyst.

The composition ratios of the metal ingredients of the catalyst calculated from the raw materials charged are illustrated by the composite oxide having the following atomic ratios.

Mo:Bi:Co:Ni:Fe:Na:Ca:B:K-:Si=12:5:2:3:0.3:0.35:0.1:0.2:0.8:12

This catalyst in an amount of 20 ml is charged into a stainless steel reaction tube provided with a jacket for a nitrate heating media and having an internal diameter of 15 mm, and raw material gas comprising 10% of propylene concentration, 17% of steam concentration and 73% of air concentration is passed through the tube with a contact period of 2.3 seconds under atmospheric pressure.

At a reaction temperature of 310° C., the following results of reaction were obtained in an actual instance of practice.
Conversion of propylene: 99.1%
Yield of acrolein: 90.8%
Yield of acrylic acid: 4.5%
Total yield: 95.3%

Comparative Example B-1

In 400 ml of pure water was dissolved 94.1 g of ammonium paramolybdate under heating. Next, 5.39 g of ferric nitrate, 25.8 g of cobalt nitrate and 38.7 g of nickel nitrate were dissolved in 60 ml of pure water under heating. These two solutions are slowly mixed with each other by thorough mixing.

To the mixed solution was added a solution in which 0.85 g of borax and 0.36 g of potassium nitrate had been dissolved in 40 ml of pure water under heating, and the mixture was amply agitated. Then, 57.6 g of bismuth subcarbonate obtained from an aqueous solution of bismuth nitrate and ammonium carbonate by the precipitation method and having no Na dissolved in solid and 32 g of silica were added to the mixture and mixed with agitation. A catalyst was thereafter produced as in Example B-1.

The composition ratios of metal components of the catalyst calculated from the raw materials charged were as follows in which the contents of Na and Ca were different from those in Example B-1.

Mo:Bi:Co:Ni:Fe:Na:Ca:B:K-:Si=12:5:2:3:0.3:0.1:0:0.2:0.08:12

Oxidation reaction of propylene was carried out under the same conditions as in Example B-1 by the use of 20 ml of the catalyst.

At a reaction temperature of 310° C., the following results of reaction were obtained.
Conversion of propylene: 95.4%
Yield of acrolein: 86.9%
Yield of acrylic acid: 5.0%
Total yield: 91.9%

Examples B-2 to B-5

The procedure of Example B-1 was followed except for the use in the catalysts of bismuth subcarbonate in which the following X, in place of Na, has been incorporated.

TABLE B-1

| | Characteristics of the Bi subcarbonate | | |
|---|---|---|---|
| Exam. No. | Na content* | X content* | Color |
| B-2 | 0.4 | Mg = 0.3 | White |
| B-3 | 0.6 | Zn = 0.3 | White |
| B-4 | 0.5 | Ce = 0.3 | Yellow |
| B-5 | 0.5 | Sm = 0.1 | White |

*content: % by weight

Evaluation of these catalysts were conducted to obtain the results set forth in the following Table B-2.

TABLE B-2

| | Evaluation of the reaction | |
|---|---|---|
| Exam. No. | Propylene conversion (%) | (Acrolein + acrylic acid) Total yield (%) |
| B-2 | 98.6 | 94.2 |
| B-3 | 98.0 | 93.9 |
| B-4 | 99.0 | 94.0 |
| B-5 | 98.8 | 93.6 |

Example B-6

In 400 ml of pure water is dissolved 94.1 g of ammonium paramolybdate under heating. Next, 5.8 g of ammonium paratangstate is added, and the mixture is agitated.

On the other hand, 18.0 g of ferric nitrate and 51.6 g of cobalt nitrate are dissolved in 60 ml of pure water under heating. These two solutions are slowly mixed with each other with ample mixing. Then, to the mixed solution is added a solution in which 0.27 g of potassium nitrate has been dissolved in 30 ml of pure water with heating, and the mixture is thoroughly agitated. Then, 11.6 g of bismuth subcarbonate in which Na and Ca have been complexed in an amount of 0.5% by weight and 0.3% by weight, respectively, and 26.9 g of colloidal silica of a SiO₂ content of 20% by weight and 4.5 g of particulate α-Al₂O₃ are added, and the mixture is mixed with agitation. In an actual instance of practice, a catalyst having the following composition was produced thereafter as in Example B-1 hereafter.

Mo:W:Bi:Co:Fe:Na:Ca:K:Si:-
(Al)=12:0.5:1:4:1:0.05:0.1:0.06:2:(5)

When 20 ml of the catalyst was subjected to the evaluation of oxidation reaction of propylene in the same manner as in Example B-1, the following results were obtained.
Conversion of propylene: 98.1%
Yield of acrolein: 89.8%
Yield of acrylic acid: 3.0%
Total yield: 92.8%

Comparative Example B-2

In 400 ml of pure water is dissolved 94.1 g of ammonium paramolybdate under heating. Next, 5.8 g of ammonium paratungstate is added, and the mixture is agitated.

On the other hand, 18.0 g of ferric nitrate, 51.6 g of cobalt nitrate and 21.5 g of bismuth nitrate are dissolved in pure water acidified by nitric acid. These two solutions are slowly mixed with each other with ample mixing.

To the mixed solution, is added a solution of 0.27 g of potassium nitrate dissolved in 30 ml of pure water under ample agitation.

Then, 26.7 g of colloidal silica of a SiO₂ content of 20% by weight and 4.5 g of particulate α-Al₂O₃ were addd with agitation.

In an actual instance of practice, a catalyst having the following composition was produced as in Example B-1 hereafter.

Mo:W:Bi:Co:Fe:K:Si:(Al)=12:0.5:1:4:1:0.06:2:5

This catalyst is different from that in Example B-1 in the type of the Bi source compound.

When 20 ml of the catlayst was subjected to the evaluation of oxidation in the same manner as in Example B-1, the following results were obtained.
Conversion of propylene: 94.2%
Yield of acrolein: 86.6%
Yield of acrylic acid: 2.9%
Total yield: 89.5%

Example C-1

In 400 ml of pure water is dissolved 94.1 g of ammonium paramolybdate under heating. Next, 7.18 g of ferric nitrate, 25.8 g of cobalt nitrate and 38.7 g of nickel nitrate are dissolved in 60 ml of pure water under heating. These two solutions are slowly mixed with each other by ample agitation.

To the mixed solution is added a solution in which 0.85 g of borax and 0.36 g of potassium nitrate have been dissolved in 60 ml of pure water under heating, and the mixture is agitated well. 64 g of granular silica is then added and the mixture is agitated. Then, 58.1 g of bismuth subcarbonate in which 0.80% by weight of Mg has been complexed is added to the mixture and mixed with agitation. Next, after heat drying of the slurry, it is subjected to thermal treatment at 300° C. for 1 hour in an air atmosphere. The particulate solid obtained is formed into tablets of 5 mm in diameter and 4 mm in height by the use of a small scale molding machine and then calcined at 500° C. for 4 hours to obtain a catalyst.

The composition ratios of the metal ingredients of the catalyst calculated from the raw materials charged are illustrated by the composite oxide having the following atomic ratios.

Mo:Bi:Co:Ni:Fe:Na:Mg:B:K-
:Si=12:5:2:3:0.4:0.1:0.4:0.2:0.08:24

This catalyst in an amount of 20 ml is charged into a stainless steel reaction tube provided with a jacket for a nitrate heating media and having an internal diameter of 15 mm, and raw material gas comprising 10% of propylene concentration, 17% of steam concentration and 73% of air concentration is passed through the tube with a contact period of 2.3 seconds under atmospheric pressure.

At a reaction temperature of 310° C., the following results of reaction were obtained in an actual instance of practice.
Conversion of propylene: 98.1%
Yield of acrolein: 90.0%
Yield of acrylic acid: 3.8%
Total yield: 93.8%

Examples C-2 to C-5

The procedure of Example C-1 was followed except for the use in the catalyst of bismuth subcarbonate in which the following X, in place of Mg, has been incorporated.

Evaluation of these catalysts were conducted to obtain the results set forth in the following Table C-2.

TABLE C-1

| | Characteristics of the Bi subcarbonate | | |
|---|---|---|---|
| Exam. No. | X | X content* | Color |
| C-2 | Ca | 1.2 | White |
| C-3 | Zn | 0.8 | White |
| C-4 | Ce | 2.0 | Yellow |
| C-5 | Sm | 2.0 | White |

*Content in % by weight

TABLE C-2

| | Evaluation of the reaction | |
|---|---|---|
| Exam. No. | Propylene conversion (%) | (Acrolein + acrylic acid) total yield (%) |
| C-2 | 98.4 | 93.8 |
| C-3 | 97.1 | 92.7 |
| C-4 | 98.1 | 93.3 |
| C-5 | 97.6 | 93.1 |

Example C-6

In 400 ml of pure water is dissolved 94.1 g of ammonium paramolybdate under heating. Next, 5.8 g of ammonium paratangstate is added, and the mixture is agitated.

On the other hand, 5.39 g of ferric nitrate, 38.7 g of cobalt nitrate and 25.8 g of nickel nitrate are dissolved in 60 ml of pure water under heating. These two solutions are slowly mixed with each other with ample mixing. Then, to the mixed solution is added a solution in which 0.85 g of borax and 0.71 g of thallium nitrate have been dissolved in 40 ml of pure water with heating, and the mixture is thoroughly agitated. Then, 58.0 g of bismuth subcarbonate in which Ca has been complexed in an amount of 1.2% by weight and 32 g of silica are added, and the mixture is mixed with agitation. In an actual instance of practice, a catalyst having the following conposition was produced thereafter as in Example C-1 hereafter.

Mo:W:Bi:Co:Ni:Fe:Na:Ca:B:Tl:Si=12:0.5:5:3:2:0.3:0.1:0.4:0.2:0.06:12

When the catalyst was subjected to the evaluation of oxidation reaction of propylene in the same manner as in Example C-1, the following results were obtained at a reaction temperature of 310° C.
Conversion of propylene: 98.1%
Yield of acrolein: 91.0%
Yield of acrylic acid: 4.1%
Total yield: 95.1%

Comp. Example C-1

In 400 ml of pure water is dissolved 94.1 g of ammonium paramolybdate under heating. Next, 7.18 g of ferric nitrate, 25.8 g of cobalt nitrate and 38.7 g of nickel nitrate are dissolved in 60 ml of pure water under heating. These two solutions are slowly mixed with each other by ample mixing.

To the mixed solution (slurry) is added a solution in which 0.85 g of borax and 0.38 g of potassium nitrate have been dissolved in 40 ml of pure water under heating, and the mixture is amply agitated. Then, 57.6 g of bismuth subcarbonate produced by precipitation method from Bi nitrate and ammonium bicarbonate and 64 g of silica are added to the mixture and mixed with agitation.

In one actual instance of practice, a catalyst was prepared according to the procedure set forth in Example C-1 which has the same composition as that in Example C-1 except for no content of Mg.

When 20 ml of the catalyst was subjected to the evaluation of oxidation reaction of propylene in the same manner as in Example C-1, the following results were obtained at a reaction temperature of 310° C.
Conversion of propylene: 95.3%
Yield of acrolein: 87.0%
Yield of acrylic acid: 4.8%
Total yield: 91.8%

We claim:

1. A process for producing a composite oxide catalyst, wherein a Mo-Bi composite oxide catalyst represented by the following formula is produced by a process comprising incorporating the compounds as respective element sources into a composite in an aqueous system and subjecting the composite to heat treatment, characterized in that use is made as a Bi source of a compound of bismuth carbonate complex of (a) Bi and Na, or (b) Bi, Na and X or (c) Bi and X which comprises at least a part of each of the required Na and/or X:

$$Mo_aBi_bCo_cNi_dFe_eNa_fX_gY_hZ_iSi_jO_k$$

wherein: X represents Mg, Ca, Zn, Ce and/or Sm; Y represents K, Rb, Cs and/or Tl; Z represents B, P, As and/or W; a–k represent atomic ratios, respectively, and when a equals 12, b=0.5 to 7, c=0 to 10, d=0 to 10, c+d=1 to 10, e=0.05 to 3, f=0.01 to 1, g=0 to 1, h=0.04 to 0.4, i=0 to 3, j=0 to 48 and k is a numeral which satisfies the oxidation state of the other elements.

2. A process for producing a composite oxide catalyst, wherein a Mo-Bi composite oxide catalyst represented by the following formula is produced by a process comprising incorporating the compounds as respective element sources into a composite in an aqueous system and subjecting the composite to heat treatment, characterized in that use is made, as a Bi source, of a compound of bismuth subcarbonate in which at least a part of the required Na has been dissolved in the solid state:

$$Mo_aBi_bCo_cNi_dFe_eNa_fY_hZ_iSi_jO_k$$

wherein: Y represents K, Rb, Cs and/or Tl; Z represents B, P, As and/or W; a–b and h–k represent atomic ratios, respectively, and when a equals 12, b=0.5 to 7, c=0 to 10, d=0 to 10, c+d=1 to 10, e=0.05 to 3, f=0.01 to 1, h=0.04 to 0.4, i=0 to 3, j=0 to 48 and k is a numeral which satisfies the oxidation state of the other elements.

3. A process according to claim 2, wherein the bismuth subcarbonate in which at least a part of required Na has been solid-dissolved is used in a form of powder.

4. A process according to claim 2, wherein in said heat treatment, said composite is heated in air and at least the greater part of the compounds as respective element sources are decomposed into a composite oxide.

5. A process according to claim 2, wherein the amount of Na dissolved in the solid state is 0.05 to 1.2% by weight to the weight of bismuth subcarbonate in which at least a part of required Na has been dissolved in the solid state.

6. A process for producing a composite oxide catalyst, wherein a Mo-Bi composite oxide catalyst represented by the following formula is produced by a process comprising incorporating the compounds as respective element sources into a composite in an aqueous system and subjecting the composite to heat treatment, characterized in that use is made as a Bi source of a compound of bismuth carbonate complex of (a) Bi, Na and X, or (b) Bi and X which comprises at least a part of each of the required Na and X or X:

$$Mo_aBi_bCo_cNi_dFe_eNa_fX_gY_hZ_iSi_jO_k$$

wherein: X represents Mg, Ca, Zn, Ce and/or Sm; Y represents K, Rb, Cs and/or Tl; Z represents B, P, As and/or W; a–k represent atomic ratios, respectively, and when a equals 12, b=0.5 to 7, c=0 to 10, d=0 to 10, c+d=1 to 10, e=0.05 to 3, f=0.01 to 1, g=0.01 to 1, h=0.04 to 0.4, i=0 to 3, j=0 to 48 and k is a numeral which satisfies the oxidation state of the other elements.

7. A process for producing a composite oxide catalyst, wherein a Mo-Bi composite oxide catalyst represented by the following formula is produced by a process comprising incorporating the compounds as respective element sources into a composite in an aqueous system and subjecting the composite to heat treatment, characterized in that use is made as a Bi source of a compound of bismuth carbonate complex of bi and X which comprises at least a part of the required X $$Mo_aBi_bCo_cNi_dFe_eNa_fX_gY_hZ_iSi_jO_k$$

wherein: X represents Mg, Ca, Zn, Ce and/or Sm; Y represents K, Rb, Cs and/or Tl; Z represents B, P, As and/or W; a-k represent atomic ratios, respectively, and when a equals 12, b=0.5 to 7, c=0 to 10, d=0 to 10, c+d=1 to 10, e=0.05 to 3, f=0 to 1, g=0.01 to 1, h=0.05 to 0.4, i=0 to 3, j=0 to 48 and k is a numeral which satisfies the oxidation state of the other elements.

* * * * *